(12) United States Patent
Lui et al.

(10) Patent No.: US 8,487,112 B2
(45) Date of Patent: Jul. 16, 2013

(54) METHOD FOR PRODUCING 4-AMINOBUT-2-ENOLIDES

(75) Inventors: Norbert Lui, Odenthal (DE); Jens-Dietmar Heinrich, Burscheid (DE)

(73) Assignee: Bayer Cropscience AG, Monheim (DE)

( * ) Notice: Subject to any disclaimer, the term of this patent is extended or adjusted under 35 U.S.C. 154(b) by 444 days.

(21) Appl. No.: 12/677,778

(22) PCT Filed: Sep. 5, 2008

(86) PCT No.: PCT/EP2008/007269
§ 371 (c)(1),
(2), (4) Date: Mar. 11, 2010

(87) PCT Pub. No.: WO2009/036898
PCT Pub. Date: Mar. 26, 2009

(65) Prior Publication Data
US 2010/0204480 A1 Aug. 12, 2010

(30) Foreign Application Priority Data
Sep. 18, 2007 (EP) ..................................... 07116638

(51) Int. Cl.
*C07D 405/12* (2006.01)
(52) U.S. Cl.
USPC .................................................... 546/283.4
(58) Field of Classification Search
None
See application file for complete search history.

(56) References Cited

U.S. PATENT DOCUMENTS

| | | | |
|---|---|---|---|
| 4,195,036 A | 3/1980 | Gozzo et al. |
| 4,468,356 A | 8/1984 | Van Sickle et al. |
| 4,748,243 A | 5/1988 | Beck et al. |
| 4,778,896 A | 10/1988 | Gallenkamp |
| 4,990,622 A | 2/1991 | Jelich |
| 5,116,993 A | 5/1992 | Jelich |
| 5,420,270 A | 5/1995 | Chandrakumar et al. |
| 5,679,796 A | 10/1997 | Kraatz |
| 6,022,974 A | 2/2000 | Werbitzky et al. |
| 6,252,087 B1 | 6/2001 | Koch et al. |
| 2009/0247551 A1 | 10/2009 | Jeschke et al. |
| 2009/0253749 A1 | 10/2009 | Jeschke et al. |
| 2010/0240705 A1 | 9/2010 | Jeschke et al. |

FOREIGN PATENT DOCUMENTS

| | | |
|---|---|---|
| CA | 1 225 094 | 8/1987 |
| CH | 503 722 | 4/1971 |
| EP | 0 123 095 A2 | 10/1984 |
| EP | 0 153 615 A1 | 9/1985 |
| EP | 0 302 389 | 2/1989 |
| EP | 0 446 913 | 9/1991 |
| EP | 0 539 588 | 5/1993 |
| EP | 0 775 700 | 5/1997 |
| EP | 0 794 180 | 9/1997 |
| JP | 05-239034 | 9/1993 |
| WO | 88/00183 | 1/1988 |
| WO | 97/10226 | 3/1997 |
| WO | 01/07414 | 2/2001 |
| WO | 2004/082616 | 9/2004 |
| WO | 2007/115643 A1 | 10/2007 |
| WO | 2007/115644 A1 | 10/2007 |
| WO | 2007/115646 A1 | 10/2007 |

OTHER PUBLICATIONS

Machine translation of relevant portions of Boehme et al. Chem. Ber. 109, 176, pp. 26-29. Obtained from <http://www.google.com/translate. on Jun. 19, 2012.*
International Preliminary Report on Patentability and Written Opinion based on International Application PCT/EP2008/007269 issued Apr. 7, 2010.
Anzini et al.; "Molecular Basis of Peripheral vs Central Benzodiazepine Receptor Selectivity in a New Class of Peripheral Benzodiazepine Receptor Ligands Related to Alpidem"; J. Med. Chem.; 1996; 39; 4275-4284.
Boehme et al.; "Kondensationsprodukte Aus Y-Chloracetessigester und Primaeren Aroma-Tischen Oder Heteroaromatischen Aminen"; Arch. Pharm. (Weinheim) 310; 26-29 (1977).
Greenhill et al.; "A New and Easier Route to Tetronic Acid"; Tetrahedron Letters No. 31; pp. 2683-2684; 1974.
Puebla et al.; "A Convenient Method for the Sysnthesis of Six-Membered Heterocyclic Enaminones"; J. Heterocyclic Chem.; 36; 1097 (1999).
Cabanal-Duvillard et al.; "A Simple Access to Key Pyridine Building Blocks"; Heterocycl. Commun. 5; 257-262 (1999).
Crossland et al.; "A Facile Synthesis of Methanesulfonate Esters"; J. Org. Chem.; vol. 35; No. 9; 1970; 3195-3196.
Eycken et al.; Synthesis of (E)-5-(2-Arylvinyl)-2-(Hetero)Arylpyridines, (E)-2-(2-Arylvinyl)-5-Methoxycarbonylpyridines and (E,E)-2,5-Bis(2-Arylvinyl)Pyridines as Polarity and Ph Probes; J. Chem. Soc. Perkin Trans 2, 2002; 928-937.
Momose et al.; 2(3H)- and 2(5H)-Furanones. III1 an Efficient Synthesis and the Eschenmoser-Mannich Reaction of N-Substituted 4-Amino-2(5H)-Furanones; Heterocycles, vol. 27, No. 8, 1988; pp. 1907-1923.
Houben-Weyl; "Methoden der Organischen Chemie", BD.; V/3; Georg Thieme Verlag Stuttgart; S. 503 und BD; V/4 S. 13; 517; 1962.
Houben-Weyl; "Methoden der Organischen Chemie"; BD XI/1; 4. AUFL. 1957; Georg Thieme Vering Stuttgart; S. 648.
Houben-Weyl; "Methoden der Organischen Chemie"; BD V/4; 1960.
Pesti et al; "Efficient Pyridinylmethyl Functionalization: Synthesis of 10,10-BIS[(2-FLUORO-4-Pyridinyl)Methyl]-9(10H)-Anthracenone (DMP 543); An Acetylcholine Release Enhancing Agent"; J. Org; Chem. 2000; 65; 7718-7722.
Mulholland et al.; A Synthesis of Tetronic Acid [Furan-2(3H),4(5H)-Dione] and Three Analogues; J. Chem. Soc., Perkins Trans. 1; 1972; NR. 9/10; pp. 1225-1231.

(Continued)

*Primary Examiner* — Alicia L Otton
(74) *Attorney, Agent, or Firm* — Baker Donelson Bearman Caldwell & Berkowitz, PC

(57) ABSTRACT

The present invention relates to a process for preparing 4-aminobut-2-enolides and also corresponding intermediates and starting compounds which are passed through or used in the process according to the invention.

3 Claims, No Drawings

OTHER PUBLICATIONS

Gassen et al.; "Fluorinated Cyclopropanecarboxylic Acids and Their Derivatives"; Journal of Fluorine Chemistry; 49 (1990) 127-139.

Shandala et al.; "Reaction of Methyl Tetronate with Some Amines. Synthesis of Substituted 4-Aminobut-2-Enolides"; J. Heterocyclic Chem.; 21; 1753-1754; Nov./Dec. 1984.

Moore; "The Leuckart Reaction" In: Organic Reactions, BD. 5; 2. AUFL; 1952, New York; John Wiley & Sons, Inc. London; pp. 300-331.

Marvel et al.; "N-Dodecyl (Lauryl) P-Toluenesulfonate"; Organic Synthesis Collective vol. 3; 1955; 366-367.

Mohacsi et al.; S(−)-A-(1-Naphthyl)Ethylamine; Organic Syntheses; 1973; 53; p. 1882.

Roos et al.; N-Butyl P-Toluenesulfonate (P-Toluenesulfonic Acid, Butyl Ester); Org. Synth.; Coll. vol. I; 1941; 145-147.

Schmidt et al.; "A Convenient Synthesis of 2,4(3H,5H)-Furandione (B-Tetronic Acid)1A"; Synthetic Communications; 11(5); 385-390 (1981).

U.S. Reissue Patent No. 28,242; Reissued Nov. 12, 1974; Boosen.

H. Boehme; "Kondensationsprodukte aus Gamma-Chloracetes-sigester und Primaeren Aromatischen Oder Heteroaromatischen Aminen"; Chem Ber; BD. 109, 1976, Seiten 26-29.

T. Momose et al; "2(3H)- and 2(5H)-Furanones. III. An Efficient Synthesis and the Eschenmoser-mannich Reaction of N-Substituted 4-Amino-2 (5H)-Furanones"; Heterocycles; BD. 27, NR. 8, 1988, Seiten 1907-1923.

M. Anzini et al.; "Molecular Basis of Peripheral vs Central Benzodiazepine Receptor Selectivity in a New Class of Peripheral Benzodiazepine Receptor Ligands Related to Alpidem"; Journal of Medicinal Chemistry. American Chemical Society, Washington, US, BD. 39, NR. 21, 1996, Seiten 4275-4284.

Puebla Pilar et al.; "A Convenient Method for the Synthesis of Six-Membered Heterocyclic Enaminones"; Journal of Heterocyclic Chemistry; Provo; UT, US, BD. 36, 1999, Seiten 1097-1100.

Campbell et al; "Synthesis of (E)- and (Z)-Pulvinones"; Journal of the Chemical Society, Perkin Transaction 1, Chemical Society. Letchworth, GB, vol. 1, 1985, pp. 1567-1576.

International Search Report based on PCT/EP2008/007270 dated Jan. 5, 2009.

European Search Report based on European Application No. 07116638 dated Apr. 7, 2008.

G. Athanasellis, O. Igglessi-Markopoulou, and J. Markopoulos, "Novel short-step synthesis of optically active tetronic acids from chiral α-hydroxy acids mediated by 1-hydroxybenzotriazole," Synlett. 2002;10:1736-1738.

* cited by examiner

METHOD FOR PRODUCING 4-AMINOBUT-2-ENOLIDES

CROSS REFERENCE TO RELATED APPLICATIONS

This application is a §371 National Stage Application of PCT/EP2008/007269 filed Sep. 5, 2008, which claims priority to European Application 07116638.3 filed Sep. 18, 2007 and European Application 07116638.3 filed Sep. 18, 2007.

BACKGROUND OF THE INVENTION

1. Field of the Invention

The present invention relates to a process for preparing 4-aminobut-2-enolides and also corresponding intermediates and starting compounds which are passed through or used in the process according to the invention. The present invention further provides processes for preparing the corresponding intermediates and starting compounds.

2. Description of Related Art

Particular substituted 4-aminobut-2-enolide compounds are known as insecticidally active compounds from EP 0 539 588 A1. In addition, patent applications WO 2007/115644, WO 2007/115643 and WO 2007/115646 also describe corresponding insecticidally active 4-aminobut-2-enolide compounds.

In general, enaminocarbonyl compounds are synthesized from tetronic acid and an amine according to scheme 1 below. This procedure is described, for example, in EP 0 539 588 A1 and in Heterocycles Vol. 27, No. 8, pages 1907 to 1923 (1988).

Scheme 1:

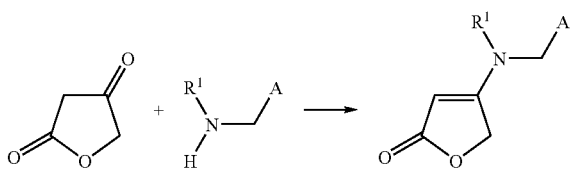

A particular disadvantage of this process is that anhydrous tetronic acid is required as a starting material, the preparation of which is inconvenient and costly.

For instance, tetronic acid is generally prepared proceeding from ethyl acetoacetate via a bromination and subsequent hydrogenation (cf. Synthetic Communication, 11(5), pages 385 to 390 (1981)). The overall yield of tetronic acid proceeding from ethyl acetoacetate is less than 40%, which makes the process relatively unattractive from an industrial point of view.

CH Patent 503 722 describes a further process for preparing tetronic acid. In this process ethyl 4-chloroacetoacetate is reacted with an aromatic amine to give 3-arylaminocrotolactone and then the tetronic acid is released by treatment with mineral acids. The disadvantage of this process is that the isolation of the tetronic acid is possible only by high-vacuum sublimation, which makes this process too relatively unattractive from an industrial point of view.

A further process for preparing tetronic acid is described in EP 0 153 615 A, in which the starting materials are 2,4-dichloroacetoacetic esters. This likewise multistage and complicated process affords the desired compound likewise only with a moderate overall yield of 65%.

Tetrahedron Letters, No. 31, pages 2683 and 2684 (1974), describes the preparation of tetronic acid and of a corresponding enaminocarbonyl compound. The synthesis described there is reproduced in scheme 2 below. The reactant used is dimethyl acetylenedicarboxylate.

Scheme 2:

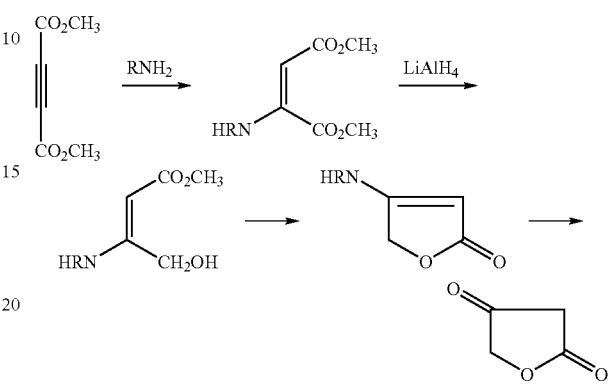

Disadvantages of this process are the low overall yield of 30% and the requirement to have to use costly reactants, for example lithium aluminium hydride (LiAlH4), as reagents.

Additionally known from the prior art is a process for preparing 4-aminobut-2-enolides proceeding from methyl tetronate (J. Heterocyclic Chem., 21, 1753 (1984)). For this process, the starting material used is the costly 4-bromo-3-methoxybut-3-enecarboxylic ester.

A further process proceeds from a 4-chloroacetoacetic ester, which is reacted with amines (Heterocycles, Vol. 27, No. 8, 1988, pages 1907 to 1923). The reaction to give the aminofuran is conducted in one step. In this step, the amine is added with glacial acetic acid to a solution of 4-chloroacetoacetic ester in benzene and the resulting mixture is heated under reflux for several hours. The yields of 4-methylamino-2(5H)-furanone in this synthesis are only 40%.

EP 0 123 095 A discloses a process in which tetronamide is prepared from 3-amino-4-acetoxycrotonic ester. 3-Amino-4-acetoxycrotonic ester is costly and inconvenient to prepare, and so an economically viable synthesis is not possible by this process.

A further process for preparing tetronic acid proceeding from malonic esters and chloroacetyl chloride is known from J. Chem, Soc., Perkin Trans. 1 (1972), No. 9/10, pages 1225 to 1231. This process affords the desired target compound with a yield of 43%.

The aforementioned international patent application WO 2007/115644 describes the preparation of 4-aminobut-2-enolides, for example of 4-[[(6-chloropyridin-3-yl)methyl](3,3-dichloroprop-2-en-1-yl)amino]furan-2(5H)-one, by reaction of 4-[[(6-chloropyridin-3-yl)methyl]amino]furan-2(5H)-one with 3-bromo-1,1-dichloroprop-1-ene (cf. preparation example, method 2, example (3)). PCT/EP2007/002386 also describes the preparation of 4-aminobut-2-enolides, for example of 4-[[(6-chloropyridin-3-yl)methyl](3,3-dichloroprop-2-en-1-yl)amino]furan-2(5H)-one by reaction of 4-[(2-fluoroethyl)amino]furan-2(5H)-one with 2-chloro-5-chloromethylpyridine (cf. preparation examples, method 3, example (4)). The reactions are preferably conducted with hydrides of lithium or of sodium. These substrates are generally costly and can simultaneously be handled only with difficulty for safety reasons. In the process according to the invention, in contrast, inexpensive bases which are simpler to handle from a safety point of view, for example NaOH, are used.

SUMMARY OF THE INVENTION

It was an object of the present invention to provide a novel, economically viable process for preparing 4-aminobut-2-enolide compounds and for preparing starting compounds for this process.

The present invention therefore provides a process for preparing compounds of the general formula (IVa) or (IVb)

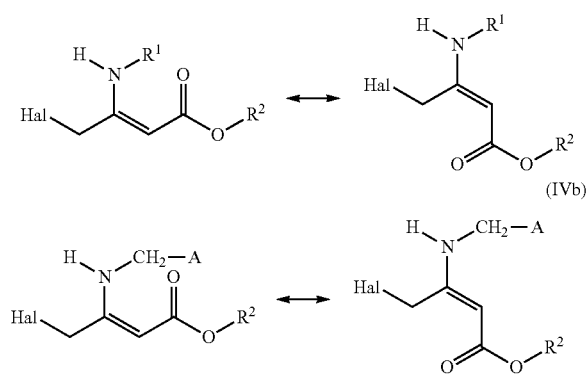

in which

A is pyrid-2-yl or pyrid-4-yl or is pyrid-3-yl which is optionally 6-substituted by fluorine, chlorine, bromine, methyl, trifluoromethyl or trifluoromethoxy or is pyridazin-3-yl which is optionally 6-substituted by chlorine or methyl or is pyrazin-3-yl or is 2-chloropyrazin-5-yl or is 1,3-thiazol-5-yl which is optionally 2-substituted by chlorine or methyl, or A is a pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl radical which is optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine) or $C_1$-$C_3$-alkylsulphonyl (which is optionally substituted by fluorine and/or chlorine), or A is a

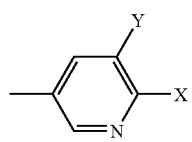

radical in which

X is halogen, alkyl or haloalkyl,

Y is halogen, alkyl, haloalkyl, haloalkoxy, azido or cyano, $R^1$ is alkyl, haloalkyl, alkenyl, haloalkenyl, alkynyl, cycloalkyl, cycloalkylalkyl, halocycloalkyl, alkoxy, alkoxyalkyl, halocycloalkylalkyl or arylalkyl, $R^2$ is $C_1$-$C_{12}$-alkyl, $C_5$-$C_8$-aryl or arylalkyl, preferably $C_1$-$C_6$ alkyl, more preferably methyl or ethyl and Hal is chlorine, bromine or iodine, characterized in that 4-haloacetoacetic esters of the general formula (II)

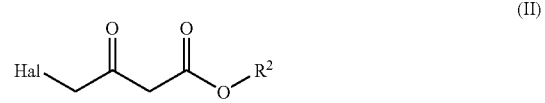

in which $R^2$ and Hal are each as defined above are reacted a) with an amine of the formula (IIIa)

in which $R^1$ is as defined above
to give the compound of the formula (IVa),
or b) with an amine of the formula (IIIb)

in which A is as defined above
to give the compound of the formula (IVb).

The present invention further provides a process for preparing 4-aminobut-2-enolides of the general formula (I)

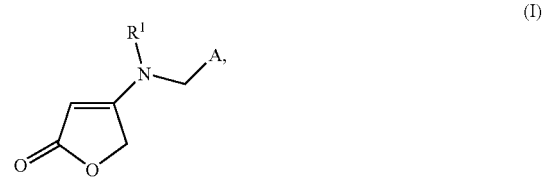

in which

A and $R^1$ are each as defined above, characterized in that 4-haloacetoacetic esters of the general formula (II)

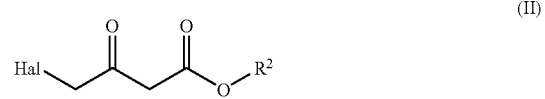

in which $R^2$ and Hal are each as defined above are reacted with a) an amine of the formula (IIIa)

in which $R^1$ is as defined above
to give a compound of the formula (IVa)

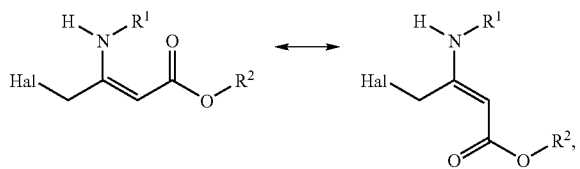
(IVa)

then the compound of the formula (IVa) is cyclized thermally in the presence of a solvent to give a compound of the formula (Va)

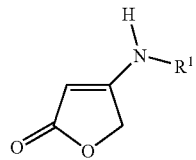
(Va)

and the compound of the formula (Va) is reacted in the last step with a compound of the formula (VIa)

(VIa)

where A is as defined above and E is a leaving group to give the compound of the formula or
b) with an amine of the formula (IIIb)

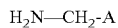
(IIIb)

in which A is as defined above
to give a compound of the formula (IVb)

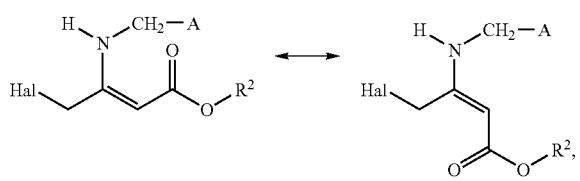
(IVb)

then the compound of the formula (IVb) is cyclized thermally in the presence of a solvent to give a compound of the formula (Vb)

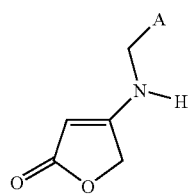
(Vb)

and the compound of the formula (Vb) is reacted in the last step with a compound of the formula (VIb)

(VIb)

where $R^1$ is as defined above and E is a leaving group to give the compound of the formula (I).

DETAILED DESCRIPTION OF A PREFERRED EMBODIMENT

Possible leaving groups E are halogen, such as chlorine, bromine or iodine, or activated hydroxyl compounds such as mesylate, tosylate or $SO_2Me$.

Surprisingly, the 4-aminobut-2-enolides of the formula (I) can be prepared under the inventive conditions with very good yields in high purity, as a result of which the process according to the invention overcomes the abovementioned disadvantages. Compared to the process known from the prior art, which proceeds from 4-chloroacetoacetic esters and reacts them with amines (Heterocycles. Vol. 27, No. 8, 1988, 1907-1923), the yields have been doubled by the process according to the invention. Compared to the process described in WO 2007/115644 for preparing 4-aminobut-2-enolides too (see above), the yield has been increased significantly by the process according to the invention.

The present invention further provides compounds of the formula (IVa) or (IVb)

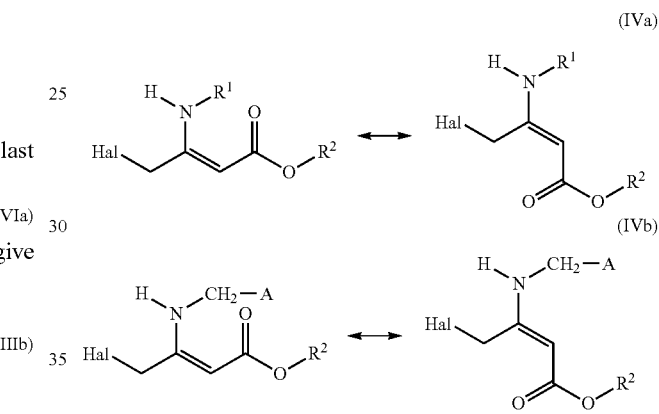

in which
Hal is chlorine and
$R^1$, A and $R^2$ are each as defined above.

The products of the process according to the invention are defined in general terms by the formula (I). Preferred, particularly preferred and very particularly preferred substituents and ranges for the radicals shown in the abovementioned formula (I) are elucidated below.

A is preferably 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl or 5-difluoromethyl-6-iodopyrid-3-yl.

$R^1$ is preferably optionally fluorine-substituted $C_1$-$C_5$-alkyl, $C_2$-$C_5$-alkenyl, $C_3$-$C_5$-cycloalkyl, $C_3$-$C_5$-cycloalkylalkyl or alkoxyalkyl.

A is more preferably the 6-fluoropyrid-3-yl, 6-chloropyrid-3-yl, 6-bromopyrid-3-yl, 6-chloro-1,4-pyridazin-3-yl, 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl radical.

$R^1$ is more preferably methyl, ethyl, propyl, vinyl, allyl, propargyl, cyclopropyl, alkoxyalkyl, 2-fluoroethyl, 2,2-difluoroethyl or 2-fluorocyclopropyl.

A is most preferably the 6-fluoropyrid-3-yl, 6-chloropyrid-3-yl, 6-bromopyrid-3-yl, 2-chloro-1,3-thiazol-5-yl, 5-fluoro-6-chloropyrid-3-yl, 5-fluoro-6-bromopyrid-3-yl or 5,6-dichloropyrid-3-yl radical.

$R^1$ is most preferably methyl, ethyl, n-propyl, n-prop-2-enyl, n-prop-2-ynyl, cyclopropyl, methoxyethyl, 2-fluoroethyl or 2,2-difluoroethyl.

The process according to the invention can be illustrated by the following schemes 3a and 3b:

Scheme 3a

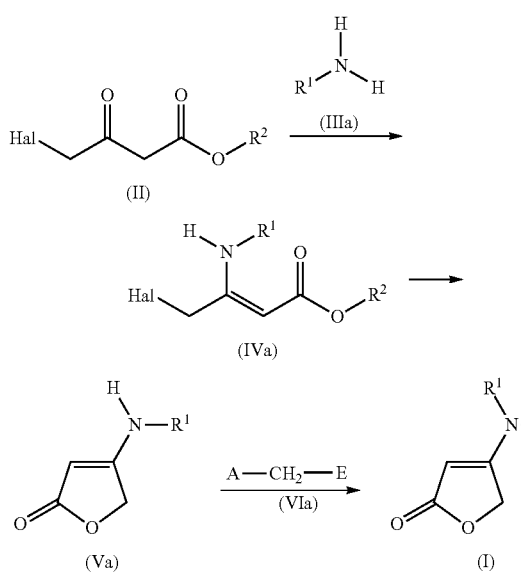

Scheme 3b

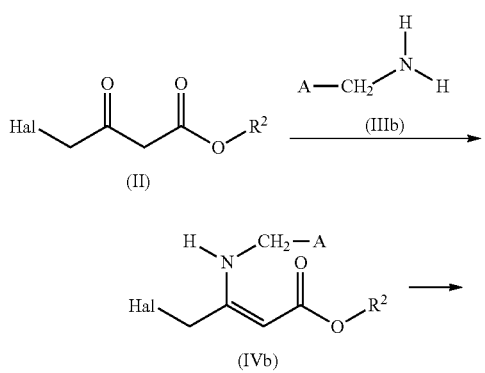

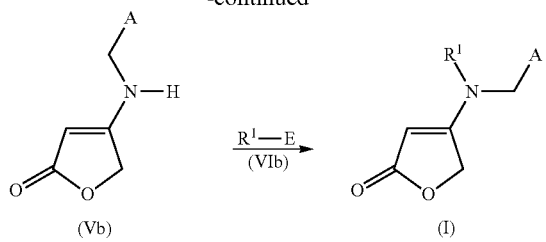

In the context of the present invention, "alkyl" is defined as linear or branched $C_{1-12}$ alkyl such as methyl, ethyl, n- or isopropyl, n-, iso-, sec- or tert-butyl, n-pentyl, n-hexyl, n-heptyl, n-octyl, n-nonyl, n-decyl, n-undecyl, n-dodecyl and others; preference is given to $C_{1-6}$ alkyl, particular preference to $C_{1-4}$ alkyl.

"Alkenyl" is defined as linear or branched $C_{2-12}$ alkenyl which has at least one double bond, such as vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl, 1,4-hexadienyl and others; preference is given to $C_{2-6}$ alkenyl, particular preference to $C_{2-4}$ alkenyl.

"Alkynyl" is defined as $C_{3-12}$ alkynyl which has at least one triple bond and optionally additionally one or more double bonds, such as ethynyl, 1-propynyl, propargyl; preference is given to $C_{3-6}$ alkynyl, particular preference to $C_{3-4}$ alkynyl.

Each alkyl constituent in the "alkoxy", "alkoxyalkyl", "cycloalkylalkyl", "halocycloalkylalkyl", "arylalkyl" radicals and similar radicals is defined as described above for "alkyl". The same applies to radicals which contain an alkenyl or alkynyl constituent.

"Cycloalkyl" is defined as $C_{3-8}$ cycloalkyl such as cyclopropyl, cyclobutyl, cyclopentyl, cyclohexyl, cycloheptyl, cyclooctyl and similar; preference is given to $C_{3-6}$ cycloalkyl.

"Aryl" is defined as an aromatic radical having 6 to 14 carbon atoms; preference is given to phenyl.

"Arylalkyl" is defined as, for example, benzyl, phenylethyl or α-methylbenzyl; preference is given to benzyl.

"Halogen" is defined as fluorine, chlorine, bromine or iodine; preference is given to fluorine or chlorine.

Each halogen constituent in the "haloalkyl", "haloalkenyl", "haloalkynyl", "halocycloalkyl", "halocycloalkylalkyl" radicals and similar radicals is defined as described above for halogen.

The 4-haloacetoacetic esters used in accordance with the present invention are compounds of the general formula (II)

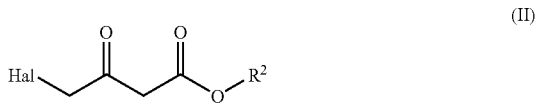

in which $R^2$ is $C_1$-$C_8$-aryl or alkylaryl, preferably $C_1$-$C_6$ alkyl, more preferably methyl or ethyl, and Hal is Cl, Br or I, preferably Cl or Br, more preferably Cl.

The 4-haloacetoacetic ester compounds are commercially available or can be prepared easily by literature methods (Organic Syntheses (1973), 53, 1882; U.S. Pat. No. 4,468, 356).

The 4-haloacetoacetic ester can be reacted with the amine of the formula (IIIa) or (IIIb) to give the compound with the formula (IVa) or (IVb) in the presence of a solvent or in bulk. Preference is given to performing the reaction in a solvent.

Suitable solvents are, for example, selected from the group consisting of aliphatic and aromatic hydrocarbons, such as n-hexane, benzene, toluene and xylene, which may be substituted by fluorine and chlorine atoms, such as methylene chloride, dichloromethane, trichloromethane, carbon tetrachloride, fluorobenzene, chlorobenzene or dichlorobenzene; ethers, such as diethyl ether, diphenyl ether, methyl tert-butyl ether, isopropyl ethyl ether, dioxane, dimethylglycol or THF; nitriles such as methyl-nitrile, butyl nitrile or phenyl nitrile; and alcohols such as ethanol or isopropanol. Preferred solvents are toluene or mixtures of toluene and ethanol.

Amines of the formula (IIIa) or (IIIb) are commercially available or can be prepared by literature methods (cf. 2-fluoroethylamine: U.S. Pat. No. 4,030,994 (1977); 3-fluoro-n-propylamine: U.S. Pat. No. 6,252,087 B1; 3,3-difluoroprop-2-enylamine hydrochloride: WO 2001/007414 A1; 3,3-dichloroprop-2-enylamine: DE 2747814; 2-chloro-2-fluorocyclopropylamine, 2,2-dichlorocyclopropylamine: K. R. Gassen, B. Baasner, J. Fluorine Chem. 49, 127-139, 1990; compounds of the formula (Ma) or (IIIb) in which $R^1$ is alkyl, primary amines: cf., for example, Houben-Weyl, Methoden der Organischen Chemie [Methods of Organic Chemistry], vol. XI/1, 4th ed. 1957, Georg Thieme Verlag Stuttgart, p. 648; M. L. Moore in "The Leuckart Reaction" in: Organic Reactions, vol. 5, 2nd ed. 1952, New York, John Wiley & Sons. Inc. London).

The compounds of the formula (IVa) and (IVb) are present in the form of an E/Z mixture.

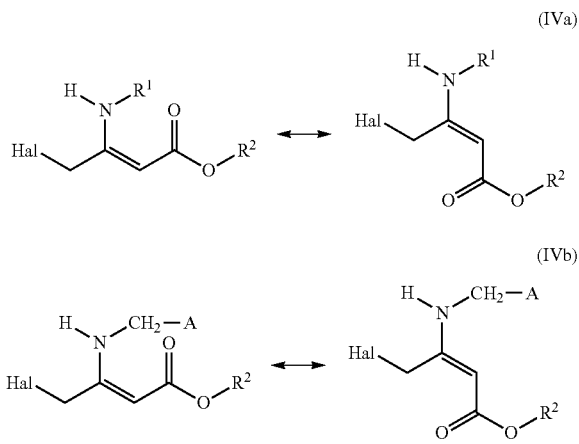

To react the compound of the formula (II) with the amine of the formula (IIIa) or (IIIb), it is optionally possible to add a Lewis acid as a catalyst. Examples thereof are acetic acid, p-toluenesulphonic acid, trifluoroacetic acid. Preference is given to using acetic acid.

The amine with the formula (III) can also be used in the form of the salt. This allows the addition of Lewis acid to be dispensed with or reduced.

The reaction of the compound of the formula (II) with the amine of the formula (IIIa) or (IIIb) can be conducted under reduced pressure, at standard pressure or under elevated pressure and at temperatures of −20° C. to 200° C.; preference is given to effecting the reaction at standard pressure and temperatures of −20° C. to 60° C., more preferably at 10° C. to 40° C., most preferably at 10° C. to 30° C. The present invention therefore also provides a process for preparing compounds of the formula (IVa) or (IVb) or for preparing compounds of the formula (I), wherein the compound of the formula (II) is reacted with the amine of the formula (IIIa) or the amine of the formula (IIIb) at −20° C. to 60° C. The reaction time is between 0.5 and 10 hours; longer reaction times do not have an adverse effect. The solvent can be removed by distilling it off or under reduced pressure in the temperature range of 20° C. to 35° C.

The cyclization of the compound of the formula (IVa) or (IVb) to the compound of the formula (Va) or (Vb) can be conducted in an inert solvent. Suitable solvents are, for example, selected from the group consisting of aliphatic and aromatic hydrocarbons, such as n-hexane, benzene, toluene and xylene, which may be substituted by fluorine and chlorine atoms, such as methylene chloride, dichloromethane, trichloromethane, carbon tetrachloride, fluorobenzene, chlorobenzene or dichlorobenzene; ethers, such as diphenyl ether, methyl tert-butyl ether, isopropyl ethyl ether, dioxane, dimethylglycol or THF; nitriles such as methyl nitrile, butyl nitrile or phenyl nitrile; toluene is preferred.

The cyclization of the compound of the formula (IVa) or (IVb) to the compound of the formula (Va) or (Vb) can be conducted under reduced pressure, at standard pressure or under elevated pressure and at temperatures of −20° C. to 200° C., preferably at 40° C.-150° C. The present invention therefore also provides a process for preparing compounds of the formula (I), wherein the compound of the formula (IVa) is thermally cyclized to the compound of the formula (Va) and the compound of the formula (IVb) is thermally cyclized to the compound of the formula (Vb) at 40° C. to 150° C. The reaction time is between 1 h and 10 hours; longer reaction times do not have an adverse effect.

The compound of the formula (Va) or (Vb) is isolated by crystallization or by removal of the solvent.

The 4-aminobut-2-enolides of the formula (I) are prepared by reacting the compound of the formula (Va) with compounds of the formula (VIa) or by reacting the compound of the formula (Vb) with compounds of the formula (VIb).

Some of the compounds of the formula (VIa) are commercially available, some of them are known and can be obtained by known methods (e.g. 2-chloro-5-chloromethyl-1,3-thiazole: DE 3 631 538 (1988), EP 446 913 (1991), EP 780 384 (1997), EP 775 700 (1997), EP 794 180 (1997), WO 9 710 226 (1997); 6-chloro-3-chloromethylpyridine: DE 3 630 046 A1 (1988), EP 373 464 A2 (1990), EP 373 464 A2 (1990), EP 393 453 A2 (1990), EP 569 947 A1 (1993); 6-chloro-3-bromomethylpyridine: I. Cabanal-Duvillard et al., Heterocycl. Commun. 5, 257-262 (1999); 6-bromo-3-chloromethylpyridine, 6-bromo-3-hydroxymethylpyridine: U.S. Pat. No. 5,420,270 A (1995); 6-fluoro-3-chloromethylpyridine: J. A. Pesti et al., J. Org. Chem. 65, 7718-7722 (2000); 6-methyl-3-chloromethylpyridine: EP 302389 A2, E. v der Eycken et al., J. Chem. Soc., Perkin Trans 2 5, 928-937 (2002); 6-trifluoromethyl-3-chloromethylpyridine: WO 2004/082616 A2; 2-chloro-5-chloromethylpyrazine: JP 05239034 A2).

General methods of preparing compounds of the formula (VIa) are reproduced in scheme 4 below.

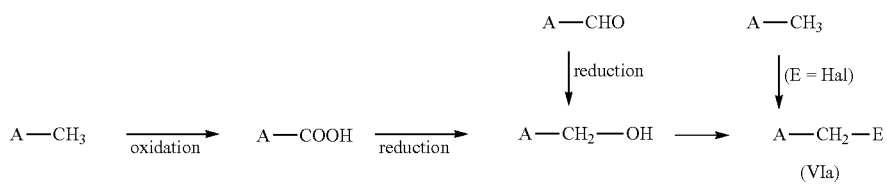

E = Hal, for example chlorine, bromine, iodine; mesylate, tosylate or SO₂Me
A = as defined above For example, the heterocyclic carboxylic acids (A-COOH) can be converted by literature methods to the corresponding heterocyclic hydroxymethyl compounds (A-CH$_2$—OD), which are subsequently converted by literature methods to activated heterocyclic hydroxymethyl compounds (A-CH$_2$-E, E=tosylate, mesylate) or heterocyclic halomethyl compounds (A-CH-E, E=Hal). The latter can also be obtained from corresponding heterocycles containing methyl groups (A-CH$_3$) using suitable halogenating agents known from the literature.

Some of the compounds of the formula (VIb) can be obtained commercially (cf., for example, chlorodifluoromethane, 1-bromo-2-fluoroethane, 2-bromo-1,1-difluoroethane, 2-bromo-1-chloro-1-fluoroethane, 1-bromo-3-fluoropropane, 3-bromo-1,1-difluoroprop-1-ene) or by literature methods (cf., for example, 3-bromo-1,1-dichloroprop-1-ene: WO 8800183 A1 (1988); compounds of the general formula (VII)) in which E is halogen, such as chlorine, bromine and iodine: Houben-Weyl, Methoden der Organischen Chemie, vol. V/3, Georg Thieme Verlag Stuttgart, p. 503 and vol. V/4 p. 13, 517; E$^1$ is mesylate: Crossland, R. K., Servis, K. L. J. Org. Chem. (1970), 35, 3195; E is tosylate: Roos, A. T. et al., Org. Synth., Coll. Vol. I, (1941), 145; Marvel, C. S., Sekera, V. C. Org. Synth., Coll. Vol. III, (1955), 366.

Suitable leaving groups E are groups which have suitable nucleofugality under the prevailing reaction conditions. By way of example, halogens, such as chlorine, bromine or iodine, or mesylate, tosylate or SO$_2$Me are specified as suitable leaving groups. Preference is given to chlorine, bromine and mesylate.

The reaction is effected preferably in the presence of a base. Suitable bases are organic and inorganic bases which are typically used in such reactions. Preference is given to using bases which are selected, by way of example, from the group consisting of hydrides, hydroxides, amides, alkoxides, acetates, fluorides, phosphates, carbonates and hydrogencarbonates of alkali metals or alkaline earth metals. Particular preference is given to sodium amide, sodium hydride, lithium diisopropylamide, sodium methoxide, potassium tert-butoxide, sodium hydroxide, potassium hydroxide, sodium acetate, sodium phosphate, potassium phosphate, potassium-fluoride, caesium fluoride, sodium carbonate, potassium carbonate, potassium hydrogen-carbonate, sodium hydrogencarbonate and caesium carbonate. Very particular preference is given to sodium hydroxide and potassium hydroxide. The present invention therefore also provides a process for preparing compounds of the formula (I), wherein the compound of the formula (Va) is reacted with the compound of the formula (VIa) to give the compound of the formula (I) and the compound of the formula (Vb) is reacted with the compound of the formula (VIb) to give the compound of the formula (I) in the presence of sodium hydroxide and potassium hydroxide. Preference is also given to tertiary amines, such as trimethylamine, triethylamine, tributylamine, N,N-dimethylaniline, N,N-dimethylbenzylamine, pyridine, alkylpyridines, such as 2-methyl-5-ethylpyridine, N-methylpiperidine, N-methylpyrrolidone, N,N-dimethylaminopyridine, diazabicyclooctane (DABCO), diazabicyclononene (DBN) and diazabicycloundecene (DBU).

The molar ratio of base to tetronamide of the formula (Va) or (Vb) used is, for example, 0.5-10, preferably 0.9-6, more preferably 1.0-2. The use of greater amounts of base is possible in principle, but does not lead to a preferred embodiment and is disadvantageous for economic reasons.

The molar ratio of alkylating agent of the formula (VIa) or (VIb) to tetronamide of the formula (Va) or (Vb) used is, for example, 0.5-3, preferably 0.9-2, more preferably 1.0-1.5. The use of greater amounts of alkylating agent is possible in principle, but does not lead to a preferred embodiment and is disadvantageous for economic reasons.

If appropriate, in the reaction of the tetronamide of the formula (Va) or (Vb) with the alkylating agent of the formula (VIa) or (VIb) a phase transfer catalyst can be used, such as quaternary ammonium or phosphonium compounds.

The tetronamide of the formula (Va) or (Vb) can be reacted with the alkylating agent of the formula (VIa) or (VIb) in bulk or in a solvent; preference is given to conducting the reaction in a solvent which is selected from customary solvents which are inert under the prevailing reaction conditions. Preference is given to aliphatic, alicyclic or aromatic hydrocarbons, such as petroleum ether, hexane, heptane, cyclohexane, methylcyclohexane, benzene, toluene, xylene or decalin; halogenated hydrocarbons, such as chlorobenzene, dichlorobenzene, dichloromethane, chloroform, carbon tetrachloride, dichloroethane or trichloroethane; ethers, such as diethyl ether, diisopropyl ether, methyl tert-butyl ether (MTBE), methyl tert-amyl ether, dioxane, tetrahydrofuran, methyl-THF, 1,2-dimethoxyethane, 1,2-diethoxyethane or anisole; nitriles, such as acetonitrile, propionitrile, n- or isobutyronitrile or benzonitrile; amides, such as N,N-di-methylformamide (DMF), N,N-dimethylacetamide, N-methylformanilide, N-methylpyrrolidone (NMP); or mixtures thereof.

The reaction of the tetronamide of the formula (Va) or (Vb) with the alkylating agent of the formula (VIa) or (VIb) can be conducted under reduced pressure, at standard pressure or under elevated pressure and at temperatures of 0° C. to 150° C.; preference is given to effecting the reaction at standard pressure and temperatures of 10 to 90° C. The reaction time is between 1 h and 30 hours; longer reaction times do not have an adverse effect.

The final purification of the 4-aminobut-2-enolides of the formula (I) can be effected by customary purification methods. Preference is given to effecting the purification by crystallization.

The present invention further provides the compounds of the formulae (IVa) and (IVb), where Hal is Cl.

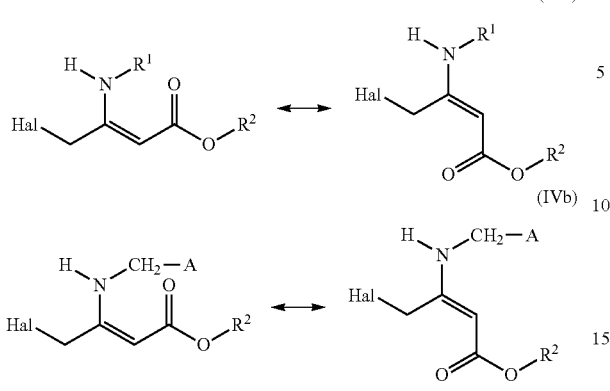

The processes according to the invention for preparing 4-aminobut-2-enolides of the formula (I) and starting materials for the preparation thereof are described in the examples which follow, which further illustrate the above description. However, the examples should not be interpreted in a restrictive manner.

PREPARATION EXAMPLES

Example 1

To a solution of 300 of ethyl 4-chloroacetoacetate in 519 ml of toluene and 200 ml of ethanol are added 20.8 ml of acetic acid. At 10° C.-30° C., with cooling, 188.7 g of a 33% methylamine solution in ethanol are added dropwise. Subsequently, the mixture is stirred at room temperature for 8 h and the solvent is removed under reduced pressure at temperatures of down to 35° C. 328 g of ethyl 4-chloro-3-(methylamino)but-2-enecarboxylate are obtained in a purity of 91% (this corresponds to 92% yield).

$^1$H NMR (CDCl$_3$, 298 K) δ: 1.25 t (3H), 3.01 d (3H), 4.00 s (1H), 4.10 q (2H), 4.67 s+4.96 s (1H) E/Z, 8.22 s (1H; NH)

Example 2

To a solution of 30 g of ethyl 4-chloroacetoacetate in 90 ml of toluene and 30 ml of ethanol are added 2 ml of acetic acid. At 10° C.-30° C., with cooling, 8.9 g of ethylamine are added dropwise. Subsequently, the mixture is stirred at room temperature for 6 h and the solvent is removed under reduced pressure at temperatures of down to 35° C. 37.7 g of ethyl 4-chloro-3-(ethylamino)but-2-enecarboxylate are obtained in a purity of 88% (this corresponds to 98% yield).

$^1$H NMR (DMSO d$_6$, 298 K) δ: 1.16 m (6H), 2.81 q+2.96 q (2H) E/Z, 3.32 q (2H), 4.32 s (2H), 4.43 s+4.70 s (1H) E/Z 8.3-9.3 broad (1H, NH)

Example 3

To a solution of 100 g of ethyl 4-chloroacetoacetate in 300 ml of toluene and 100 ml of ethanol are added 7 ml of acetic acid. At 10° C.-30° C., with cooling, 37.3 g of n-propylamine are added dropwise. Subsequently, the mixture is stirred at room temperature for 9 h and the solvent is removed under reduced pressure at temperatures of down to 35° C. 140.6 g of ethyl 4-chloro-3-(n-propylamino)but-2-enecarboxylate are obtained in a purity of 76% (this corresponds to 88% yield).

$^1$H NMR (DMSO d$_6$, 298 K) δ: 0.92 t (3H), 1.16 t (3H), 1.56 m (2H), 3.26 q (2H), 4.00 m (2H), 4.31 s (2H), 4.44 s+4.72 s (1H) E/Z, 7.7-8.8 broad (1H, NH)

Example 4

To a solution of 100 g of ethyl 4-chloroacetoacetate in 300 ml of toluene and 100 ml of ethanol are added 7 ml of acetic acid. At 10° C.-30° C., with cooling, 38.3 g of isopropylamine are added dropwise. Subsequently, the mixture is stirred at room temperature for 5 h and the solvent is removed under reduced pressure at temperatures of down to 35° C. 141.8 g of ethyl 4-chloro-3-(isopropylamino)but-2-enecarboxylate are obtained in a purity of 70% (this corresponds to 82% yield).

$^1$H NMR (DMSO d$_6$, 298 K) δ: 1.16 t (3H), 1.21 d (6H), 3.26 q (2H), 4.00 m (1H), 4.34 s (2H), 4.44 s+4.69 s (1H) E/Z, 7.7-9.0 broad (1H, NH)

Example 5

To a solution of 100 g of ethyl 4-chloroacetoacetate in 300 ml of toluene and 100 ml of ethanol are added 6.7 ml of acetic acid. At 10° C.-30° C., with cooling, 48.3 g of n-butylamine are added dropwise. Subsequently, the mixture is stirred at room temperature for 8 h and the solvent is removed under reduced pressure at temperatures of down to 35° C. 136.6 g of ethyl 4-chloro-3-(n-butylamino)but-2-enecarboxylate are obtained in a purity of 89% (this corresponds to 94% yield).

$^1$H NMR (DMSO d$_6$, 298 K) δ: 0.92 t (3H), 1.16 t (3H), 1.35 m (2H), 1.52 m (2H), 3.29 q (2H), 4.01 m (2H), 4.44 s+4.72 s (1H) E/Z, 7.7-8.5 broad (1H, NH)

Example 6

To a solution of 100 g of ethyl 4-chloroacetoacetate in 300 ml of toluene and 100 ml of ethanol are added 6.7 ml of acetic acid. At 10° C.-30° C., with cooling, 47.4 g of isobutylamine are added dropwise. Subsequently, the mixture is stirred at room temperature for 8 h and the solvent is removed under reduced pressure at temperatures of down to 35° C. 140.8 g of ethyl 4-chloro-3-(isobutylamino)but-2-enecarboxylate are obtained in a purity of 79% (this corresponds to 86% yield).

$^1$H NMR (DMSO d$_6$, 298 K) δ: 0.91 t (3H), 0.93 t (3H), 1.17 t (3H), 1.78 m (1H), 3.12 t (2H), 4.02 q (2H), 4.31 s (2H), 4.44 s+4.69 s (1H) E/Z, 8.0-8.5 broad (1H, NH)

Example 7

To a solution of 100 g of ethyl 4-chloroacetoacetate in 300 ml of toluene and 100 ml of ethanol are added 6.7 ml of acetic acid. At 10° C.-30° C., with cooling, 46.5 g of 2-methoxyethylamine are added dropwise. Subsequently, the mixture is stirred at room temperature for 8 h and the solvent is removed under reduced pressure at temperatures of down to 35° C. 140.8 g of ethyl 4-chloro-3-(2-methoxyethylamino)but-2-enecarboxylate are obtained in a purity of 88% (this corresponds to 95% yield).

$^1$H NMR (DMSO d$_6$, 298 K) δ: 1.16 t (3H), 3.27 d (2H), 3.37 s (3H), 3.46 d (2H), 3.99 m (2H), 4.32 s (2H), 4.49 s+4.72 s (1H) E/Z, 7.7-8.5 broad (1H, NH)

Example 8

To a solution of 100 g of ethyl 4-chloroacetoacetate in 300 ml of toluene and 100 ml of ethanol are added 6.7 ml of acetic acid. At 10° C.-30° C., with cooling, 65.7 g of benzylamine are added dropwise. Subsequently, the mixture is stirred at room temperature for 8 h and the solvent is removed under reduced pressure at temperatures of down to 35° C. 157.8 g of ethyl 4-chloro-3-(benzylamino)but-2-enecarboxylate are obtained in a purity of 50% (this corresponds to 52% yield).

$^1$H NMR (DMSO d$_6$, 298 K) δ: 1.11 it (3H), 3.95 q (2H), 4.24 d (2H), 4.34 s (2H), 4.44 s+4.72 s (1H) E/Z, 7.20-7.40 m (5H), 8.3-8.8 broad (1H, NH)

Example 9

To a solution of 2.1 g of ethyl 4-chloroacetoacetate in 12 ml of toluene is added 0.15 ml of acetic acid. At 10° C.-30° C., with cooling, 2 g of 2-chloro-5-(aminomethyl)pyridine dissolved in 4 ml of ethanol are added dropwise. Subsequently, the mixture is stirred at room temperature for 8 h and the solvent is removed under reduced pressure at temperatures of down to 35° C. 4.2 g of ethyl 4-chloro-3-([[6-chloropyridin-3-yl]methyl]amino)but-2-enecarboxylate are obtained in a purity of 86% (this corresponds to 98% yield).

$^1$H NMR (CDCl$_3$, 298 K) δ: 1.26 t (3H), 3.98 s (2H), 4.13 q (2H), 4.56 d (2H), 4.79 s+4.99 s (1H) E/Z, 7.35 d (1H), 7.64 d (1H), 8.35 d (1H), 8.5-8.7 broad (1H, NH)

Example 10

To a solution of 197.2 g of ethyl 4-chloroacetoacetate in 1080 ml of toluene are added 13.3 ml of acetic acid. At 10° C.-30° C., with cooling, 100 g of 2,2-difluoroethylamine dissolved in 360 ml of ethanol are added dropwise. Subsequently, the mixture is stirred at room temperature for 8 h and the solvent is removed under reduced pressure at temperatures of down to 35° C. 278 g of ethyl 4-chloro-3-(2,2-difluoroethylamino)but-2-enecarboxylate are obtained in a purity of 93% (this corresponds to 98% yield).

$^1$H NMR (DMSO d$_6$, 298 K) δ: 1.17 t 3H), 3.73 m (2H), 4.04 q (2H), 4.36 s (2H), 4.84 s (1H), 6.03 t+6.16 t+6.31 t (1H, CHF$_2$), 8.2-8.4 t (broad) (1H, NH)

Example 11

328.8 of ethyl 4-chloro-3-(methylamino)but-2-enecarboxylate (Example 1) are suspended in 519 g of toluene and the suspension is heated under reflux for 4 h. Subsequently, the suspension is cooled to 20° C., and the solids are filtered off and washed with 150 ml of toluene and with 150 ml of ethanol. 142 g of 4-(methylamino)furan-2(5H)-one are obtained with a purity of 95% (this corresponds to 71% yield).

$^1$H NMR (DMSO d$_6$, 298 K) δ: 2.71 d (3H), 4.50 s (1H), 4.60 s (2H): 7.2-7.7 broad (1H, NH)

Example 12

37.5 g of ethyl 4-chloro-3-(ethylamino)but-2-enecarboxylate (Example 2) are suspended in 86.5 g of toluene and heated under reflux for 2 h. Subsequently, the mixture is cooled to 20° C. and the solvent is removed under reduced pressure. 25.5 g of 4-(ethylamino)furan-2(5H)-one are obtained with a purity of 74% (this corresponds to 75% yield).

$^1$H NMR (DMSO d$_6$, 298 K) δ: 1.12 t (3H), 3.07 m (2H), 4.51 s (H), 4.60 s (2H), 7.4-7.7 broad (1H, NH)

Example 13

140 g of ethyl 4-chloro-3-(n-propylamino)but-2-enecarboxylate (Example 3) are dissolved in 216 g of toluene and the solution is heated under reflux for 2 h. Subsequently, the mixture is cooled to 20° C. and the solvent is removed under reduced pressure. 100.3 g of 4-(n-propylamino)furan-2(5H)-one are obtained with a purity of 86% (this corresponds to 89% yield).

$^1$H NMR (DMSO d, 298 K) δ: 0.89 t (3H), 1.51 no (2H), 3.00 q (2H), 4.52 s (1H), 4.60 s (1H), 7.4-7.6 broad (1H, NH)

Example 14

50 g of ethyl 4-chloro-3-(n-butylamino)but-2-enecarboxylate (Example 5) are dissolved in 86 g of toluene and the solution is heated under reflux for 2 h. Subsequently, the mixture is cooled to 20° C. and the solvent is removed under reduced pressure. 40.7 g of 4-(n-butylamino)furan-2(5H)-one are obtained with a purity of 86% (this corresponds to 99% yield).

$^1$H NMR (DMSO d$_6$, 298 K) δ: 0.89 t (3H), 1.33 m (2H), 1.50 m (2H), 3.01 q (2H), 4.51 s (1H), 4.59 s (2H), 7.4-7.7 broad (H, NH)

Example 15

140 g of ethyl 4-chloro-3-(isobutylamino)but-2-enecarboxylate (Example 6) are dissolved in 216 g of toluene and the solution is heated under reflux for 2 h. Subsequently, the mixture is cooled to 20° C. and the solvent is removed under reduced pressure. 104 g of 4-(isobutyl-amino)furan-2(5H)-one are obtained with a purity of 87% (this corresponds to 92% yield).

$^1$H NMR (DMSO d$_6$, 298 K) δ: 0.89 d (6H), 1.79 m (1H), 2.84 t (2H), 4.52 s (1H), 4.61 s (2H), 7.4-7.7 broad (1H, NH)

Example 16

157 g of ethyl 4-chloro-3-(benzylamino)but-2-enecarboxylate (Example 8) are dissolved in 259 g of toluene and the solution is heated under reflux for 4 h. Subsequently, the mixture is cooled to 20° C., and the solids are filtered off and washed with 100 ml of toluene. 109 g of 4-(benzylamino)furan-2(5H)-one are obtained with a purity of 92% (this corresponds to 86% yield).

$^1$H NMR (DMSO d$_6$, 298 K) δ: 4.27 d (2H), 4.58 s (1H), 4.67 s (2H), 7.26-7.45 m (5H), 7.9-8.2 broad (1H, NH)

Example 17

18.8 g of ethyl 4-chloro-3-([[6-chloropyridin-3-yl]methyl]amino)but-2-enecarboxylate (Example 9) are dissolved in 86 g of toluene and the solution is heated under reflux for 9 h. Subsequently, the mixture is cooled to 20° C. and the solvent is removed under reduced pressure. 16.1 g of 4-([[6-chloropyridin-3-yl]methyl]amino)furan-2(5H)-one are obtained with a purity of 96% (this corresponds to 87% yield).

$^1$H NMR (CDCl$_3$, 298 K) δ: 4.33 d (2H), 4.66 s (1H), 4.72 s (2H), 6.5-6.7 broad (1H, NH), 7.32 d (1H), 7.63 d (1H), 8.34 d (1H)

Example 18

280 g of ethyl 4-chloro-3-(2,2-difluoroethylamino)but-2-enecarboxylate (Example 10) are dissolved in 709 g of toluene and the solution is heated under reflux for 4 h. Subsequently, the mixture is cooled to 20° C., and the solids are filtered off and washed with 100 ml of toluene. 183 g of 4-(difluoroethylamino)furan-2(5H)-one are obtained with a purity of 97% (this corresponds to 96% yield).

17

¹H NMR (DMSO d₆, 298 K) δ: 3.44-3.59 m (2H), 4.65 s (1H), 4.77 s (2H), 6.60 t+6.14 t+6.28 t (1H, CHF₂), 7.4-7.9 broad (1H, NH)

Example 19

30 g of 4-(methylamino)furan-2(5H)-one (Example 11) are initially charged in 450 ml of dimethoxyethane at room temperature. Subsequently, 12.6 g of sodium hydroxide are added and, at 40° C., 225 g of a 20% solution of 2-chloro-5-(chloromethyl)pyridine in dimethoxyethane are metered in. The mixture is stirred at 50° C. for a further 6 h. The solvent is substantially removed under reduced pressure and the residue is admixed with 300 ml of water. The solids are filtered off, washed with 150 ml of water and dried under reduced pressure. 58.7 g of 4-([[6-chloropyridin-3-yl]methyl](methyl)amino)furan-2(5H)-one are obtained with a purity of 94% (this corresponds to 87% yield).

¹H NMR (DMSO d₆, 298 K) δ: 2.88 s (3H), 4.47 s (2H), 4.74 s (1H), 4.89 s (2H), 7.52 d (1H), 7.78 d (1H), 8.37 s (1H)

Example 20

6.3 g of 4-(benzylamino)furan-2(5H)-one (Example 16) are initially charged in 75 ml of dimethoxyethane at room temperature. Subsequently, 1.1 g of sodium hydroxide are added and, at 40° C. 25.5 g of a 20% solution of 2-chloro-5-(chloromethyl)pyridine in dimethoxyethane are metered in. The mixture is stirred at 50° C. for a further 6 h. The solvent is substantially removed under reduced pressure and the residue is admixed with 50 ml of water and 50 ml of methylene chloride. The organic phase is removed, and the aqueous phase is extracted once again with 50 ml of methylene chloride. The combined methylene chloride phases are dried over sodium sulphate and the solvent is removed under reduced pressure. 8 g of 4-{benzyl[(6-chloropyridin-3-yl)methyl]amino}furan-2(5H)-one are obtained (this corresponds to 85% yield).

¹H NMR (acetonitrile-d₃) δ: 4.40 (s, 4H), 4.71 (s, 1H) 4.87 (s, 2H) 7.23 (d, J=7.37 Hz, 2H) 7.28-7.33 (m, 1H) 7.33-7.38 (m, 3H) 7.61 (dd, J=8.25, 2.64 Hz, 1H) 8.20 (d, J=2.20 Hz, 1H)

Example 21

6.3 g of 4-(benzylamino)furan-2(5H)-one (Example 16) are initially charged in 75 ml of dimethoxyethane at room temperature. Subsequently, 1.3 g of sodium hydroxide are added and, at 40° C., 34.4 g of a 15% solution of 2-chloro-5-(chloromethyl)-1,3-thiazole in dimethoxyethane are metered in. The mixture is stirred at 50° C. for a further 6 h. The solvent is substantially removed under reduced pressure and the residue is admixed with 50 ml of water and 50 ml of methylene chloride. The organic phase is removed, and the aqueous phase is extracted once again with 50 ml of methylene chloride. The combined methylene chloride phases are dried over sodium sulphate and the solvent is removed under reduced pressure. 6.9 g of 4-{benzyl[(2-chloro-1,3-thiazol-5-yl)methyl]amino}furan-2(5H)-one are obtained (this corresponds to 71% yield).

Example 22

6.3 g of 4-(benzylamino)furan-2(5H)-one (Example 16) are initially charged in 75 ml of dimethoxyethane at room temperature. Subsequently, 1.1 g of sodium hydroxide are added and, at 40° C., 4 g of benzyl chloride are metered in. The mixture is stirred at 50° C. for a further 7 h. The solvent is substantially removed under reduced pressure and the residue is admixed with 50 ml of water and 50 ml of methylene chloride. The organic phase is removed, and the aqueous phase is extracted once again with 50 ml of methylene chloride. The combined methylene chloride phases are dried over sodium sulphate and the solvent is removed under reduced pressure. 5.6 g of 4-(dibenzylamino)furan-2(5H)-one are obtained (this corresponds to 68% yield).

The invention claimed is:

1. A process for preparing an 4-aminobut-2-enolide of formula (I)

(I)

in which

A is pyrid-2-yl or pyrid-4-yl or is pyrid-3-yl which is optionally 6-substituted by fluorine, chlorine, bromine, methyl, trifluoromethyl or trifluoromethoxy, or is a radical
in which
X is halogen, alkyl or haloalkyl, and
Y is halogen, alkyl, haloalkyl, haloalkoxy, azido or cyano, and
R¹ is alkyl, haloalkyl, alkenyl, haloalkenyl, alkynyl, cycloalkyl, cycloalkylalkyl, halocycloalkyl, alkoxy, alkoxyalkyl, halocycloalkylalkyl or arylalkyl,
comprising reacting a 4-haloacetoacetic ester of formula (II)

(II)

in which
R² is $C_1$-$C_{12}$-alkyl, $C_5$-$C_8$-aryl or arylalkyl, and
Hal is Cl, Br or I,
in the presence of a solvent at a temperature of from −20° C. to 60° C.,
a) with an amine of formula (IIIa)

(IIIa)

in which $R^1$ is as defined above,
to give a compound of formula (IVa)

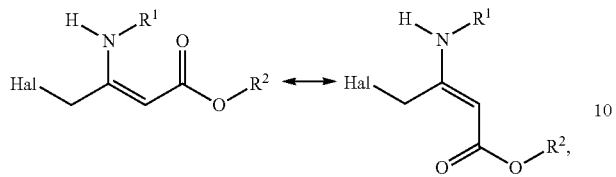

(IVa)

followed by
removing the solvent by distillation or under reduced pressure in a temperature range of from 20° C. to 35° C.,
thermally cyclizing the compound of formula (IVa) in the presence of a solvent at a temperature of from 40° C. to 150° C. to give a compound of formula (Va)

(Va)

isolating the compound of formula (Va) by crystallization or removal of solvent, and reacting the compound of formula (Va) with a compound of the formula (VIa)

A-CH$_2$-E  (VIa)

where A is as defined above and E is a leaving group selected from the group consisting of chlorine, bromine, iodine, mesylate, tosylate, or SO$_2$CH$_3$,
to give compound (I);
or
b) with an amine of formula (IIIb)

H$_2$N-CH$_2$-A  (IIIb)

in which A is as defined above,
to give a compound of formula (IVb)

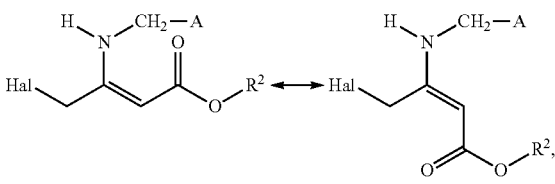

(IVb)

followed by
removing the solvent by distillation or under reduced pressure in a temperature range of from 20° C. to 35° C.,
thermally cyclizing the compound of formula (IVb) in the presence of a solvent at a temperature of from 40° C. to 150° C. to give a compound of formula (Vb)

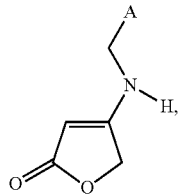

(Vb)

isolating the compound of formula (Vb) by crystallization or removal of solvent, and reacting the compound of formula (Vb) with a compound of formula (VIb)

$R^1$-E  (VIb)

where $R^1$ is as defined above and E is a leaving group selected from the group consisting of chlorine, bromine, iodine, mesylate, tosylate, or SO$_2$CH$_3$,
to give compound (I).

2. A process according to claim 1 wherein the reaction of the compound of formula (Va) with the compound of formula (VIa) or the reaction of the compound of formula (Vb) with the compound of formula (VIb) is carried out in the presence of a base.

3. A process according to claim 2 wherein the base is sodium hydroxide or potassium hydroxide.

* * * * *